(12) United States Patent
Kishimoto et al.

(10) Patent No.: US 6,514,725 B1
(45) Date of Patent: Feb. 4, 2003

(54) STAT FUNCTION-REGULATORY PROTEIN

(75) Inventors: Tadamitsu Kishimoto, 5-31, Nakanocho 3-chome, Tondabayashi-shi, Osaka 584-0021 (JP); Tetsuji Naka, Suita (JP)

(73) Assignee: Tadamitsu Kishimoto, Osaka (JP)

( * ) Notice: Subject to any disclaimer, the term of this patent is extended or adjusted under 35 U.S.C. 154(b) by 0 days.

(21) Appl. No.: 09/341,349

(22) PCT Filed: Oct. 23, 1997

(86) PCT No.: PCT/JP97/03860

§ 371 (c)(1),
(2), (4) Date: Jul. 9, 1999

(87) PCT Pub. No.: WO98/30688

PCT Pub. Date: Jul. 16, 1998

(30) Foreign Application Priority Data

Oct. 1, 1997 (JP) .............................................. 9-014737

(51) Int. Cl.[7] .......................... C12N 15/12; C12N 5/00; C12N 5/06; G01N 33/53; C07H 21/04
(52) U.S. Cl. ........................ 435/69.1; 435/7.8; 435/7.2; 435/320.1; 435/325; 435/352.3; 530/350; 536/23.1; 536/23.5
(58) Field of Search ........................ 435/7.2, 7.8, 69.1, 435/252.3, 320.1, 325; 530/350; 536/23.1, 23.5

(56) References Cited

PUBLICATIONS

Stratagene Catalogue, 1991, p. 66.*
Starr R, et al. A family of cytokine–inducible inhibitors of signalling. Nature. 1997 Jun. 26;387(6636):917–921.*
Mikayama T. Molecular cloning and functional expression of a cDNA encoding glycosylation–inhibiting factor. Proc. Natl. Acad. Sci. USA vol. 90, pp. 10056–10060, 1993.*
Voet et al. Biochemistry. 1990. John Wiley & Sons, Inc. pp. 126–128 and 228–234.*
Naka T. et al. Structure and function of a new STAT–Induced STAT–Inhibitor. Nature. 1997. Jun. 26;387(6636)924–929.*
Schluter G, et al. Sequence Analysis of the Conserved Protamine Gene Cluster Shows That it Contains a Fourth Expressed Gene. Mol. Reprod. Dev. 43(1):1–6. 1996.*
Endo et al. *Nature*, vol. 387, pp. 921–924, (1997).
Schlüter et al. *Molecular Reproduction and Development*, vol. 43, pp. 1–6, (1996).
Yoshimura et al. *The EMBO Journal*, vol. 14, No. 12, pp. 2816–2826, (1995).
Starr et al. *Nature*, vol. 387, pp. 917–921, (1997).
A. Takaho et al., Nature (Jun., 1997) vol. 387 p.921–924.
T. Naka et al., Nature (Jun., 1997) vol. 387 p. 924–929.
S. Minamoto et al., Biochem. Biophys. Res. Commun. (Aug., 1997) vol. 237 p. 79–83.
S. Groger et al., Mol. Reprod. Dev. (1996) vol. 43, No. 1, p. 1–6.
A. Yoshimura et al., ENBO J. (1995) vol. 14, No. 12, p. 2816–2826.
K. Ohya et al., J. Biol. Chem. (Oct., 1997) vol. 272, No. 43, p.27178–27182.
S. Robyn et al., Nature (Jun., 1997) vol. 387, p.917–921.

* cited by examiner

*Primary Examiner*—Prema Mertz
*Assistant Examiner*—Joseph F. Murphy
(74) *Attorney, Agent, or Firm*—Birch, Stewart, Kolasch & Birch, LLP

(57) ABSTRACT

Disclosed is a protein having the ability to inhibit the function of a STAT in a mammalian JAK/STAT signal transduction pathway, which is induced by STAT3 or STAT6, which has the ability to inhibit tyrosine phosphorylation of gp130 or STAT3 and which comprises an SH2 domain; and also disclosed is a DNA coding for the same. Further disclosed is a method for screening a substance having the capability to regulate cytokine activity, in which the protein of the present invention is used. Still further disclosed are an antisense DNA and an antisense RNA capable of inhibiting the biosynthesis of the above-mentioned protein; a monoclonal antibody capable of binding to the above-mentioned protein; and a DNA probe and an RNA probe capable of hybridizing to the above-mentioned DNA. Still further disclosed are a replicable recombinant DNA molecule comprising a replicable expression vector and, operably inserted therein, the DNA of the present invention; a cell of a microorganism or cell culture, transformed with the replicable recombinant DNA molecule; and a method for screening a substance having the capability to regulate cytokine activity in which the transformant is used.

11 Claims, 9 Drawing Sheets

Fig. 1

```
ggccccTcgagtaggatggtagcacgcaaccaggtggcagccgacaatgcgatctccc
                               M   V   A   R   N   Q   V   A   A   D   N   A   I   S   P cggcagcagagccccgacggcggtcagagccctcctcgtcctcgtcttcgtcctcgccag
  A   A   E   P   R   R   R   S   E   P   S   S   S   S   S   S   S   P   A cggcccccgtgcgtccccggccctgcccgggggtcccagccccagccctggcgacactc
  A   P   V   R   P   R   P   C   P   G   V   P   A   P   A   P   G   D   T   H acttccgcaccttccgctcccactccgattaccggcgcatcacgcggaccagcgcgctcc
  F   R   T   F   R   S   H   S   D   Y   R   R   I   T   R   T   S   A   L   L tggacgcctgcggcttctattggggaccc ctgagcgtgcacggggcgcacgagcggctgc
  D   A   C   G   *F*  *Y*  *W*  *G*  *P*  *L*  *S*  *V*  *H*  *G*  *A*  *H*  *E*  *R*  *L*  *R* gtgccgagcccgtgggcaccttcttggtgcgcgacagtcgccaacggaactgcttcttcg
  *A*  *E*  *P*  *V*  *G*  *T*  *F*  *L*  *V*  *R*  *D*  *S*  *R*  *Q*  *R*  *N*  *C*  *F*  *F*  *A* cgctcagcgtgaagatggcttcgggccccacgagcatccgcgtgcacttccaggccggcc
  *L*  *S*  *V*  *K*  *M*  *A*  *S*  *G*  *P*  *T*  *S*  *I*  *R*  *V*  *H*  *F*  *Q*  *A*  *G*  *R* gcttccacttggacggcaaccgcgagaccttcgactgccttttcgagctgctggagcact
  *F*  *H*  *L*  *D*  *G*  *N*  *R*  *E*  *T*  *F*  *D*  *C*  *L*  *F*  *E*  *L*  *L*  *E*  *H*  *Y* acgtggcggcgccgcgccgcatgttgggggccccgctgcgccagcgccgcgtgcggccgc
  *V*  *A*  *A*  *P*  *R*  *R*  *M*  *L*  *G*  *A*  *P*  *L*  R   Q   R   R   V   R   P   L tgcaggagctgtgtcgccagcgcatcgtggccgccgtgggtcgcgagaacctggcgcgca
  Q   E   L   C   R   Q   R   I   V   A   A   V   G   R   E   N   L   A   R   I tccctcttaacccggtactccgtgactacctgagttccttccccttccagatctgaccgg
  P   L   N   P   V   L   R   D   Y   L   S   S   F   P   F   Q   I   *
ctgccgctgtgccgcagcattaagtgggggcgccttattatttcttattattaattatta ttattttctggaaccacgtgggagccctccccgcctgggtcggagggagtggttgtgga gggtgagatgcctcccacttctggctggagacctcatcccacctctcagggggtgggggtg ctcccctcctggtgctccctccgggtcccccctggttgtagcagcttgtgtctggggcca ggacctgaattccactcctacctctccatgtttacatattcccagtatctttgcacaaac cagggtcggggagggtctctggcttcattttctgctgtgcagaatatcctattttata tttttacagccagtttaggtaataaactttattatgaaagtttttttttaaaagaaacaa acaaagatt
```

Fig. 2

```
CIS     WYWGSITASEARQHLQKMPEGTFLVRDSTHPSYLFTLSVKTTRGPTNVRIEYADSSFRL
        ***.....*.....*.********........*.****..*.****.....*.*
SIIS-1  GFYWGPLSVHGAHERLRAEPVGTFLVRDSRQRNCFFALSVKMASGPTSIRVHFQAGRFHL
STAT 3  G     G    S          L  P GTFLLRFS
STAT 6  G     S             L  P GTFLLRFS                    S

CIS     DSNCLSRPRILAFPDVVSLVQHYVASCAADTRSDSPD
        *.*....*.*....*.*****.
SIIS-1  DGN-----RE-TFDCLFELLEHYVAAPRRMLGAPL
STAT 3         D                  A
STAT 6         D       L
```

STAT FUNCTION-REGULATORY PROTEIN

This application is the national phase under 35 U.S.C. § 371 of PCT International Application No. PCT/JP97/03860 which has an International filing date of Oct. 23, 1997, which designated the United States of America.

BACKGROUND OF THE INVENTION

1. Field of the Invention

The present invention relates to a STAT-induced STAT inhibitor. More particularly, the present invention is concerned with a protein having the ability to inhibit the function of a STAT protein in a mammalian JAK/STAT signal transduction pathway and a DNA coding for the same. The protein of the present invention is induced by STAT3 or STAT6, and has the ability to inhibit tyrosine phosphorylation of gp130 and STAT3, and it comprises an SH2 domain. The protein of the present invention can be advantageously used for screening a novel substance having the capability to regulate cytokine activity. The present invention is also concerned with an antisense DNA and an antisense RNA which are capable of inhibiting the biosynthesis of the above-mentioned protein; a monoclonal antibody capable of binding to the above-mentioned protein; a DNA probe and an RNA probe which are capable of hybridizing to the above-mentioned DNA; a replicable recombinant DNA molecule comprising a replicable expression vector and, operably inserted therein, the above-mentioned DNA; and a cell of a microorganism or cell culture, transformed with the replicable recombinant DNA molecule. Furthermore, the transformant of the present invention can also be used for screening a novel substance having the capability to regulate cytokine activity.

2. Prior Art

Proteinaceous chemical substances which participate in intercellular signal transduction are called cytokines. Various substances, such as interferons, interleukins and colony-stimulating factors, have been identified as cytokines. Cytokines are glycoproteins, and it is generally known that receptors specific for cytokines are expressed on the surface of a target cell for the cytokines and physiological activities of the cytokines (such as regulation of cell proliferation and differentiation) are exerted only upon occurrence of binding between the cytokines and the receptor molecules.

Elucidation of an intercellular signal transduction pathway of a cytokine and clarification of a control mechanism thereof are very important. The elucidation and clarification may possibly lead to a development of a novel pharmaceutical or therapeutic method. The signal transduction mechanisms of cytokines have been elucidated in recent studies. Most of the cytokine receptors consist of two or three polypeptide chains, namely a ligand-specific receptor chain and a signal transducer that is commonly used by various cytokines {see FASEB J. 6, 3387–3396 (1992); and Cell 69, 1121–1132 (1992)}. The nature of this receptor system explains the functional redundancy of cytokines. For example, Takeda et al. {Molecular Medicine vol. 33, extra edition, Meneki (Immunity) 1996–97, ii} disclose that a JAK kinase (Janus kinase) having tyrosine phosphorylation activity is bound to an intracellular domain of a cytokine receptor. Binding of the cytokine (which is a ligand) to the receptor induces the dimerization of the receptor components and, as a consequence, two receptor-associated JAK kinases move toward each other and mutually activate each other. As a result, the two JAK kinases themselves and the cytokine receptor are phosphorylated.

In this situation, the STAT (signal transducer and activator of transcription) protein in the cell binds to the phosphorylated cytokine receptor, and it transmits a signal from the cytokine bound to the cell membrane via receptor to target genes in the cell nucleus. gp130 is a component protein of various receptors, such as IL-6 (interleukin-6) receptor, IL-11 (interleukin-11) receptor and LIF (leukemia inhibitory factor) receptor, and it is known that the binding of a cytokine to a receptor results in the activation of a JAK kinase, which in turn phosphorylates gp130. A STAT binds to the phosphorylated gp130 and signal transduction occurs consequently.

A STAT protein is a protein identified in recent studies, and six different types of STAT proteins (STAT1 to STAT6) are known in the art. Signal transduction from a STAT protein to a target gene in the cell nucleus takes place in the following manner. The binding of the above-mentioned ligand (namely a cytokine) to the receptor activates a JAK kinase, and the activated JAK kinase phosphorylates the tyrosine residue of the STAT protein. Next, the phosphorylated STAT protein forms a homodimer with the same type of STAT, or forms a heterodimer with a different type of STAT. The resultant STAT homodimer or heterodimer is capable of transducing the signals from the cytokines to the genes in the cell nucleus, and thus, the STAT is activated. The activated STAT translocates to the target gene and binds to a specific site on the gene, thereby initiating RNA synthesis, followed by biosynthesis of a new protein.

Homo- or heterodimerization of ligand-binding receptor components (i.e., a ligand-receptor complex, namely, a complex composed of two receptor molecules each binding a ligand thereto) stimulates a unique cytokine signalling cascade {see Cell 80, 213–223 (1995)}, i.e., the JAK/STAT pathway {see Science 264, 1415–1421 (1994); Nature 377, 591–594 (1995); and Cell 84, 331–334 (1996)}, which subsequently induces the activation of target genes. However, little is known about the genes (targets) of which the expression is directly induced by the STAT family proteins. One feature of cytokines is the transient expression of their activity, which suggests that a negative feedback regulation operates in the cytokine-signal transduction. Only a few proteins which can exert this negative feedback regulation are known in the art. Examples of known proteins include:

(i) an SH2-domain-containing phosphotyrosine phosphatase (SHP-1) which associates with the tyrosine-phosphorylated IL-3 receptor β-chain and with erythropoietin receptor (EPO-R) {see Cell 85, 15 (1996); Mol. Cell. Biol. 13, 7577–7586 (1993); and Cell 80, 729–738 (1995)}; and (ii) a cytokine-inducible-SH2-containing protein (CIS) which binds to the STAT5-binding sites of EPO-R {see EMBO J. 14, 2816–2826 (1995); and ditto 15, 2425–2433 (1996)}.

As is apparent from the above, the target genes of the STAT family proteins, and the feedback mechanisms responsible for switching off the cytokine signals have not been fully elucidated.

Therefore, the present inventors made an attempt to isolate a protein encoded by a novel gene which regulates the STAT signals, and to elucidate a novel feedback mechanism responsible for switching off the cytokine signals.

It is an object of the present invention to identify a novel protein regulating the STAT signals, and to provide a method for utilizing the novel protein in the field of medicine. It is another object of the present invention to provide a protein encoded by the STAT target gene (that is, a gene whose expression is induced by the STAT) which is capable of inhibiting the STAT activity, and also to provide a method for utilizing the novel protein in the field of medicine.

SUMMARY OF THE INVENTION

The inventors of the present invention have made extensive and intensive studies with a view toward isolating a gene which regulates the STAT signals and analyzing the functions thereof. Particularly, the present inventors prepared a monoclonal antibody against the known, highly conserved sequence motif GTFLLRFS (SEQ ID NO: 5 (Gly-Thr-Phe-Leu-Leu-Arg-Phe-Ser in 3-letter abbreviation) found in an SH2 (src homology-2) domain which is important for the signal transduction of STAT1 to STAT6 (the above-mentioned sequence is a phosphotyrosine recognition site of the SH2 domain). A murine thymus cDNA library consisting of 3 million bacteriophage plaques was screened using the prepared monoclonal antibody, and about twenty unknown genes (excluding the known genes, such as the genes encoding STAT3 and the like) were isolated.

The whole sequences of five of the isolated genes were determined, and two genes were found to contain an SH2 domain. One of these genes was later identified as a gene encoding CIS protein (cytokine inducible SH2-containing protein). The other gene was a novel gene encoding a protein consisting of 212 amino acids, and having an SH2 domain at the C-terminal region and a domain consisting of eight contiguous serine residues at the N-terminal region. Further studies have revealed that this novel protein, in general, is induced by gp130-transduced signalling pathways. A northern blot analysis confirmed that the novel gene is not expressed in the cells transfected with a dominant-negative form of STAT3 gene which is incapable of being tyrosine phosphorylated by a JAK kinase (the cells were transfected with STAT3 gene in which a tyrosine at the 705th residue is substituted by phenylalanine). In addition, the amino acid sequence was deduced from the nucleotide sequence of the novel gene, and the amino acid sequence of SEQ ID NO: 2 was obtained. The present inventors named the protein encoded by the novel gene "SIIS-1" (abbreviation for "STAT-induced inhibitor of STAT function-1"). From the analysis of SIIS-1 in factor-dependent cell lines, it has become apparent that SIIS-1 is also induced by STAT6, and the results of immunoblotting with anti-phosphotyrosine monoclonal antibody revealed that SIIS-1 has the ability to inhibit the tyrosine phosphorylation of gp130 and STAT3.

Therefore, it is a principal object of the present invention to provide a substantially pure protein having the ability to inhibit the function of a STAT protein in a mammalian JAK/STAT signal transduction pathway, wherein the protein has the following characteristics:

(1) the protein is induced by STAT3 or STAT6;
(2) the protein has the ability to inhibit tyrosine phosphorylation of gp130 and STAT3; and
(3) the protein comprises an SH2 domain.

It is another object of the present invention to provide a DNA coding for the above-mentioned protein, particularly, the DNA having the nucleotide sequence of SEQ ID NO: 1.

It is still another object of the present invention to provide a method for screening a substance which can be advantageously used as a pharmaceutical or a diagnostic reagent, which comprises contacting a sample with the above-mentioned protein, and assessing the activation or inhibition of the protein by the substance as a criterion.

Still a further object of the present invention is to provide an antisense DNA and an antisense RNA capable of inhibiting the biosynthesis of the above-mentioned protein, a monoclonal antibody capable of binding to the above-mentioned protein, or a DNA probe and an RNA probe capable of hybridizing to the above-mentioned DNA.

Still a further object of the present invention is to provide a replicable recombinant DNA molecule, comprising a replicable expression vector and, operably inserted therein, a gene encoding SIIS-1; and a cell of a microorganism or cell culture, transformed with the replicable recombinant DNA.

Still a further object of the present invention is to provide a method for screening a substance having the capability to regulate cytokine activity in which the transformant is used.

The foregoing and other objects, features and advantages of the present invention will be apparent to those skilled in the art from the following detailed description and the appended claims taken in connection with the accompanying sequence listing and drawings.

BRIEF DESCRIPTION OF THE SEQUENCE LISTING

SEQ ID NO: 1 is the nucleotide sequence (SEQ ID NO: 2) of the novel STAT inhibitor protein of the present invention. SEQ ID NO: 2 is the amino acid sequence of the novel STAT inhibitor protein of the present invention.

BRIEF DESCRIPTION OF THE DRAWINGS

In the accompanying drawings:

FIG. 1 is a nucleotide sequence and deduced amino acid sequence of SIIS-1 cDNA, and the asterisk indicates a stop codon and the underlined portion indicates the SH2 domain;

FIG. 2 shows an alignment of a sequence of the SH2 domain of SIIS-1 (SEQ ID NO: 3) with those of CIS, (SEQ ID NO: 4) STAT3 and STAT6, and the asterisks indicate the amino acid residues that are identical in CIS and SIIS-1, and the underlined portion indicates the phosphotyrosine recognition site;

DETAILED DESCRIPTION OF THE INVENTION

Figure 3:
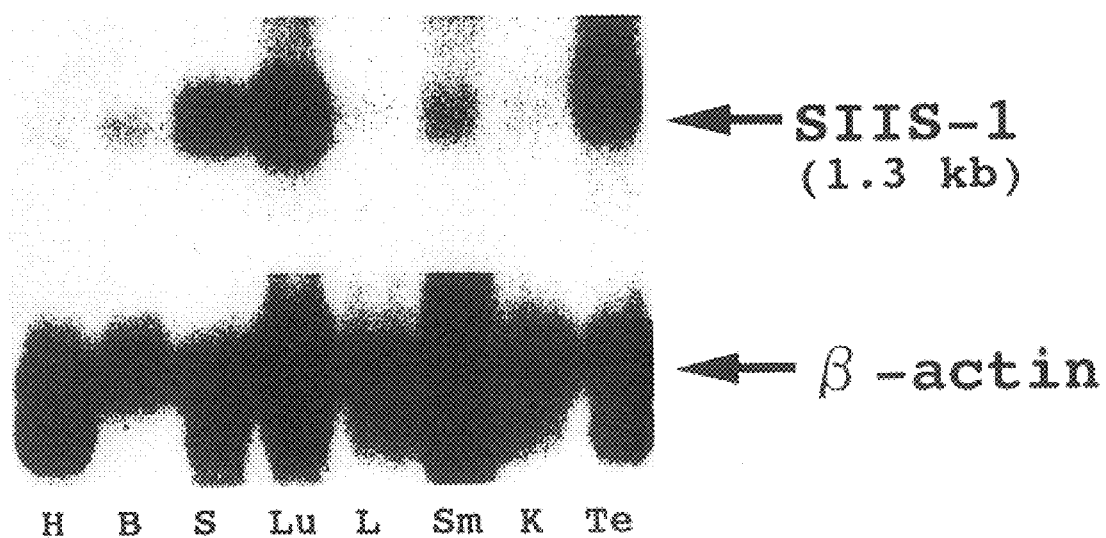
FIG. 3 shows the expression of SIIS-1 mRNA in various murine tissues, and in FIG. 3, H represents heart, B represents brain, S represents spleen, Lu represents lung, L represents liver, Sm represents skeletal muscle, K represents kidney and Te represents testis.

According to the present invention, there is provided a novel protein capable of inhibiting the function of a STAT protein and a gene coding for the same.

For easy understanding of the present invention, the essential features and various preferred embodiments of the present invention are enumerated below.

1. A substantially pure protein having the ability to inhibit the function of a STAT (signal transducer and activator of transcription) protein in a mammalian JAK/STAT signal transduction pathway, wherein the protein has the following characteristics:
   (1) the protein is induced by STAT3 or STAT6;
   (2) the protein has the ability to inhibit tyrosine phosphorylation of gp130 and STAT3; and
   (3) the protein comprises an SH2 domain.
2. The protein according to item 1, wherein the protein comprises a contiguous sequence of at least 150 amino acids of an amino acid sequence having at least 40% homology to the 212 amino acid sequence of SEQ ID NO: 2.
3. The protein according to item 2, wherein the protein has the amino acid sequence of SEQ ID NO: 2.
4. An isolated DNA coding for the protein of any one of items 1 to 3.
5. The DNA according to item 4, wherein the nucleotide sequence has the nucleotide sequence of SEQ ID NO: 1.
6. A method for screening a substance having the capability to regulate cytokine activity, which comprises:
   contacting a sample with the protein of any one of items 1 to 3;
   assessing the activation or inhibition of the protein by the substance; and
   screening the substance by using the activation or inhibition as a criterion.
7. An antisense DNA capable of inhibiting the biosynthesis of the protein of any one of items 1 to 3.
8. An antisense RNA capable of inhibiting the biosynthesis of the protein of any one of items 1 to 3.
9. A monoclonal antibody capable of binding to the protein of any one of items 1 to 3.
10. A DNA probe capable of hybridizing to the DNA of item 4 or 5.
11. An RNA probe capable of hybridizing to the DNA of item 4 or 5.
12. A replicable recombinant DNA molecule, comprising a replicable expression vector and, operably inserted therein, the DNA of item 4 or 5.
13. A cell of a microorganism or cell culture, transformed with the replicable recombinant DNA of item 12.
14. A method for screening a substance having the capability to regulate cytokine activity, which comprises:
   contacting a sample with the transformed cell of a microorganism or cell culture of item 13;
   assessing the activation or inhibition of a protein by the substance, wherein the protein is encoded by the replicable recombinant DNA molecule in the transformed cell; and
   screening the substance by using the activation or inhibition as a criterion.

Hereinbelow, the present invention is described in detail.

In the present invention, with respect to the nucleotide sequences, A represents adenine, C represents cytosine, G represents guanine and T represents thymine.

In the present invention, with respect to the amino acid sequences, A represents an alanine residue, R represents an arginine residue, N represents an asparagine residue, D represents an aspartic acid residue, C represents a cysteine residue, Q represents a glutamine residue, E represents a glutamic acid residue, G represents a glycine residue, H represents a histidine residue, I represents an isoleucine residue, L represents a leucine residue, K represents a lysine residue, M represents a methionine residue; F represents a phenylalanine residue, P represents a proline residue, S represents a serine residue, T represents a threonine residue, W represents a tryptophan residue, Y represents a tyrosine residue and V represents a valine residue.

In the present invention, the present inventors have cloned a cDNA encoding an SH2 domain-containing protein which is inducible by STAT3 and inhibits STAT3 function. Particularly, for the purpose of cloning a novel member of STAT family, the present inventors prepared a monoclonal antibody against a partial amino acid sequence (GTFLLRFS) (SEQ ID NO:5) of the SH2 domain, which is a phosphotyrosine recognition site of STAT3 {see Science 267, 1347–1349 (1995)}. A murine thymus cDNA library was screened using the prepared monoclonal antibody and 20 unknown genes were isolated. Two of the isolated genes contained an SH2 domain, and one gene was identified as a gene coding for a known protein called CIS {see EMBO J. 14, 2816–2826 (1995)}. The other gene was a novel gene, and the protein encoded by this gene was named "SIIS-1" by the present inventors.

SIIS-1 cDNA has a single open reading frame encoding a 212-amino acid polypeptide which contains an SH2 domain in the middle (at codons 79 to 167) of the sequence. No other consensus motifs, such as SH3 domain, were found in the SIIS-1 (see FIG. 1, wherein the asterisk indicates the stop codon and the underlined portion indicates the SH2 domain). The SH2 domain of SIIS-1 showed some homology to that of CIS (amino acid sequence homology: 36%), but with the exception of the phosphotyrosine recognition site present in the SH2 domain {see Cell 77, 63–71 (1994); Science 264, 95–98 (1994); and Science 265, 1701–1706 (1994)}, no significant homology was found between the amino acid sequence of the SH2 domain of SIIS-1 and that of STAT3 or STAT6 (see FIG. 2, wherein the asterisks indicate the amino acid residues that are identical in CIS and SIIS-1, and the underlined portion indicates the phosphotyrosine recognition site).

SIIS-1 expression in various murine tissues was examined. As apparent from FIG. 3, it was found that SIIS-1 mRNA expressed ubiquitously in murine tissues, with the expression being strong in lung, spleen and testis, and weak in all other tissues.

Further, the present inventors analyzed the possibility of SIIS-1 induction in several factor-dependent cell lines.

Myeloma MH60 cells and murine myeloid leukemia M1 cells (hereinafter, frequently referred to as "M1") both expressed SIIS-1 mRNA by a treatment with IL-6 plus soluble IL-6 receptor (sIL-6R) (see FIG. 4). In addition, IL-4-dependent cells (CT4S cells) {see J. Immunol. 142, 800–807 (1989)} and G-CSF (granulocyte colony-stimulating factor)-dependent cells (NFS60 cells) expressed SIIS-1 mRNA in response to IL-4 and G-CSF, respectively. These results show that SIIS-1 is induced not only by IL-6 and G-CSF, both of which activate STAT3 {see Blood 84, 1760–1764 (1994)}, but also by IL-4, which is a cytokine capable of activating STAT6 {see Science 265, 1701–1706 (1994)}. The present inventors have previously reported that the promoter region of the SIIS-1 gene contains STAT3 and STAT6 binding sequence {see Cell 77, 63–71(1994) and EMBO J. 14, 2527–2535 (1995)}, and this report is consistent with the above-mentioned findings.

The present inventors analyzed the SIIS-1 induction in M1 cells transfected with wild-type STAT3 gene (hereinafter, frequently referred to as "M1-STAT3") and M1 cells transfected with Y705F gene {dominant-negative form of STAT3 in which the tyrosine residue (705th a.a.) to be phosphorylated by JAK kinase is substituted by a phenylalanine residue (expression of this inactive mutant is dominant over wild-type)} (hereinafter, frequently referred to as "M1-Y705F").

In the analysis, transfectants containing only the neomycin-resistance gene (hereinafter, frequently referred to as "M1-Neo") were used as a control. As a result, it was found that SIIS-1 mRNA was more strongly induced by LIF in M1-STAT3 cells than in the control M1-Neo cells, and was not induced in M1-Y705F cells (see FIG. 5). These results indicate that the SIIS-1 gene is one of the target genes of STAT3 and is induced by the JAK/STAT pathway.

Next, the effects of SIIS-1 on the gp130 -transduced signalling pathway were analyzed. M1 transfectants (or clones) constitutively expressing wild-type SIIS-1 (SH+) and M1 transfectants constitutively expressing a mutant SIIS-1 (SH−) which is truncated at the C-terminal region containing the SH2 domain were individually established by the present inventors for conducting the analyses. The results of the analyses revealed that the M1-Neo cells and the mutant SIIS-1 (SH−) clones were affected by LIF as observed in the case of the parental M1 cells, that is, the cells underwent growth arrest and cell death after the treatment with LIF (see FIG. 6), and the dead cells showed features of apoptosis, such as chromatin condensation and apoptotic bodies {see FIGS. 8(a) to 8(c)}. In contrast, the growth of wild-type SIIS-1 (SH+) clones did not arrest following the stimulation with LIF {see FIGS. 6, 7 and 8 (d)}. These results suggest that SIIS-1 blocks the gp130 -transduced signalling pathway, and the SH2 domain of SIIS-1 is required for this blocking of the signalling pathway.

Further, the present inventors analyzed the inhibitory mechanism of SIIS-1 on the gp130 -transduced signalling pathway. That is, the present inventors stimulated various cells with IL-6 plus sIL-6R {see Science 267, 1349–1353 (1995); and Blood 86, 1243–1254 (1995)}, and measured the tyrosine phosphorylations of gp130 and STAT3 in the stimulated cells. As apparent from FIG. 9, tyrosine phosphorylations of gp130 and STAT3 were much reduced in wild type SIIS-1 (SH+) clones, as compared to those in the control M1-Neo cells and the mutant SIIS-1 (SH−) clones.

From the results of the analyses mentioned above, it became apparent that the protein which the present inventors successfully isolated, purified and cloned in the present invention was SIIS-1, which is an SH2 domain-containing protein induced by STAT3 or STAT6, and inhibits the tyrosine phosphorylation of gp130 and STAT3.

CIS is a protein known to participate in the negative-feedback regulation of the JAK/STAT signalling pathway {see EMBO J. 14, 2816–2826 (1995) and ditto 15, 2425–2433 (1996)}, and it inhibits STAT5 function by directly associating with the STAT5-binding region of the EPO receptor. The inhibitory mechanism of SIIS-1 in the JAK/STAT pathway is quite different from that of CIS. SIIS-1 reduces the tyrosine phosphorylation of STAT3 and gp130 which is a receptor component participating in the signal transduction.

The studies of the present inventors suggest that the tyrosine phosphorylation of gp130 is a prerequisite for its association with SIIS-1 at the STAT3-binding region and, therefore, SIIS-1 is unlikely to compete with STAT3 for binding to gp130. SIIS-1 is likely to block the signal transduction in a step earlier than that of CIS in the JAK/STAT signalling pathway, that is, by binding to the JAK kinase.

Another interesting feature of SIIS-1 is that SIIS-1 is not induced by all types of STATs and, therefore, SIIS-1 should be distinguished from general inhibitors of the JAK/STAT pathway.

The SIIS-1 cDNA of the present invention can be prepared using various cells and there is no particular limitation with respect to the types of cells, but preferably, use is made of a commercially available cDNA library of animal cells. With respect to a method for purifying the DNA of the present invention, it is preferably performed by preparing a monoclonal antibody against the highly conserved amino acid sequence found in the SH2 domain (i.e., GTFLLRFS) using a customary method, and isolating the DNA by using the prepared monoclonal antibody by means of a commercially available immunoscreening kit.

With respect to the protein of the present invention, there is no particular limitation as long as the protein is a substantially pure protein having the above-mentioned functions of SIIS-1. Therefore, the amino acid sequence of the protein is not limited to the sequence of SEQ ID NO: 2, and examples of proteins include a partial sequence of SEQ ID NO: 2 and a sequence comprising an amino acid sequence which is homologous to the sequence of SEQ ID NO: 2. In the present invention, a "partial sequence" is a contiguous sequence of at least 150 amino acids comprising an SH2 domain. In addition, this sequence has at least 40% homology to the amino acid sequence of SEQ ID NO: 2. In the present invention, a "homologous sequence" is an amino acid sequence having at least 40% homology to the amino acid sequence of SEQ ID NO: 2 and having the ability to inhibit the function of a STAT in a mammalian JAK/STAT signalling pathway in the same manner as SIIS-1. A homologous sequence can be obtained by partially changing the amino acid sequence by substitution, deletion or insertion, and such a change may occur by natural or artificial mutation.

One of the characteristic features of the protein of the present invention is that this protein is induced by either STAT3 or STAT6. This characteristic of SIIS-1 can be confirmed in the isolated protein. In general, the genetic information of a certain protein can be obtained from a database when the amino acid sequence of the protein is established in the art. On the other hand, when the amino acid sequence of a certain protein is unknown, the genetic information of the protein can be obtained as follows. First, the amino acid sequence of the protein is determined, and then, a gene encoding the protein is cloned by using the obtained amino acid sequence information. Subsequently, a probe capable of specifically detecting the mRNA of the protein is designed. Whether or not an mRNA of a particular protein is induced by STAT3 or STAT6 can be confirmed, for example, by a northern blot analysis performed in Example 4. That is, when the mRNA of the protein is induced in M1 cells transfected with STAT3, but not induced in M1 cells transfected with a dominant-negative form of STAT3, it can be concluded that the protein is induced by STAT2.

With respect to the DNA of the present invention, there is no particular limitation as long as the DNA encodes a protein having the above-mentioned functions of SIIS-1. Therefore, the nucleotide sequence of the DNA of the present invention is not limited to the DNA sequence of SEQ ID NO: 1, and examples of DNAs include a nucleotide sequence encoding an amino acid sequence which comprises a partial sequence of an amino acid sequence having at least 40% homology to SEQ ID NO: 2. In addition, as long as the nucleotide sequence encodes an amino acid sequence having the functions of SIIS-1, the DNA of the present invention may be a partial nucleotide sequence of SEQ ID NO: 1, and a nucleotide sequence comprising the partial nucleotide sequence.

In another aspect of the present invention, there is provided a method for screening a novel substance having the capability to regulate cytokine activity, in which the above-mentioned SIIS-1 protein is used. By using the screening method of the present invention, it becomes possible to screen a novel pharmaceutical having a novel cytokine regulatory activity, namely, SIIS-1 inhibitory activity or SIIS-1-like or SIIS-1 activity promoting activity.

There is no particular limitation with respect to the method for screening a substance having the capability to regulate cytokine activity by using the protein of the present invention. For example, a specific system for measuring the effects of the substance on SIIS-1 activity can be constructed using the protein, and the constructed system can be used for the screening method. By way of illustration, for example, a substance which inhibits the activity of SIIS-1 can be obtained by the screening method.

With respect to a sample substance used for screening a substance having SIIS-1 inhibitory activity or SIIS-1-like or SIIS-1 activity promoting activity, there is no particular limitation as long as the substance is not cytotoxic. For example, either a high molecular compound or an orally administrable low molecular compound can be used as the sample substance. An orally administrable low molecular compound obtained by the screening method can be used as a novel pharmaceutical having SIIS-1 inhibitory activity or SIIS-1-like or SIIS-1 activity promoting activity.

In still another aspect of the present invention, either an antisense DNA or an antisense RNA which is capable of inhibiting the biosynthesis of the STAT inhibitor protein are provided. The antisense DNA or antisense RNA for the gene encoding SIIS-1 of the present invention can be used as a potentiator for an endogenous or administered cytokine in the same manner as G-CSF (which is used for treating congenital/idiopathic neutropenia, and neutropenia resulting from a bone marrow transplantation or chemotherapy for treating cancer) and IL-6 (which is under development as a pharmaceutical for thrombocytopenia, and thrombocytopenia resulting from chemotherapy for treating cancer).

Based on the nucleotide sequence of a DNA encoding SIIS-1, an antisense DNA or RNA specific for the SIIS-1 DNA of the present invention can be designed with ease. Further, the effects of the antisense DNA or RNA can be confirmed by using the cells which express wild-type SIIS-1 (SH+). By way of illustration, an antisense DNA or RNA is applied to the cells expressing wild-type SIIS-1 (SH+) which have been cultured in the presence of LIF. The effectiveness of the antisense DNA or RNA is substantiated when the cells experience growth arrest, inhibition of DNA synthesis and apoptosis and when a customary western blotting analysis using an anti-SIIS-1 antibody reveals an inhibition of the biosynthesis of the SIIS-1 protein.

In a further aspect of the present invention, there is provided a monoclonal antibody against the STAT inhibitor protein. The monoclonal antibody of the present invention can be used for diagnosis.

With respect to the method for obtaining the monoclonal antibody of the present invention, there is no particular limitation, but the monoclonal antibody can be advantageously obtained by using the isolated SIIS-1 protein by a customary method for preparing a monoclonal antibody, such as a cell fusion method. With respect to the amino acid sequence used for preparing the antibody, there is no particular limitation, but a contiguous sequence of at least 6 amino acids is preferably used. By using the monoclonal antibody of the present invention, it becomes possible to construct a system for detecting the SIIS-1 protein in cells or tissues by ELISA or RIA, or western blotting. Such a system for detecting the SIIS-1 protein can be used for diagnosis.

In still a further aspect of the present invention, a DNA probe and an RNA probe specific for SIIS-1 mRNA are provided. The SIIS-1 mRNA-specific probes can be used to detect expression of the SIIS-1 gene in cells and tissues and, thus, a diagnostic assay can be conducted using the probe of the present invention. A DNA to be used as a probe can be designed with ease, based on the nucleotide sequence of the SIIS-1 gene of the present invention and the conventional rule of base pairing (A and T form a pair, and C and G form another pair).

With respect to the nucleotide sequence of the probe of the present invention, there is no particular limitation as long as the probe is capable of hybridizing to the DNA of the present invention. By way of illustration, not only the nucleotide sequence of SEQ ID NO: 1, which is the whole cDNA sequence encoding the SIIS-1 protein, but also a partial sequence thereof can be used as the probe. With respect to a method for conducting diagnosis with the probes, the hybridization techniques described in Examples below, such as northern hybridization, can be employed.

In the present invention, there is no particular limitation with respect to an expression vector used for preparing a replicable recombinant DNA molecule, and use can be made of a conventional expression vector which is customarily used in the art. Examples of replicable recombinant DNA molecules of the present invention include pEF-BOS/SIIS-1 (SH+). pEF-BOS/SIIS-1 (SH+) is a replicable recombinant DNA molecule obtained by inserting the SIIS-1 gene into the cloning site of the expression vector pEF-BOS, and by using the SIIS-1 gene of the present invention, such a recombinant DNA molecule can be constructed by the method described in Example 1 below. By way of illustration, the SIIS-1 cDNA is digested with restriction enzymes XbaI and PvuII, and the end of the obtained restriction fragment (XbaI-PvuII) is converted into a blunt end. Subsequently, the resultant blunt-ended fragment is inserted into the blunt-ended XbaI cleavage site of the expression vector pEF-BOS. The thus prepared recombinant DNA molecule of the present invention is preferably transformed into conventional host cells.

In the present invention, with respect to a cell of a microorganism or cell culture which is to be used as a host cell, there is no particular limitation as long as the cell is capable of expressing the recombinant DNA of the present invention and synthesizing the SIIS-1 protein. For example, M1 cells can be transformed (transfected) with the above-mentioned pEF-BOS/SIIS-1 (SH+) by electroporation. The transformed cell of the present invention can be used for the above-mentioned screening of a novel substance having the capability to regulate cytokine activity. Further, the transformants can be used to express the recombinant DNA molecule of the present invention to thereby synthesize the protein, and the synthesized protein can be extracted therefrom to be used for screening a novel substance having the capability to regulate cytokine activity or for preparing a monoclonal antibody capable of binding to the protein of the present invention.

In still a further aspect of the present invention, there is provided a method for screening a novel substance having the capability to regulate cytokine activity, in which a cell of a microorganism or cell culture, transformed with a DNA encoding SIIS-1 is used. Like the above-mentioned screening method using the protein of the present invention, a novel pharmaceutical having the novel cytokine regulatory activity, namely, the SIIS-1 inhibitory activity or the SIIS-1-like or SIIS-1 activity promoting activity, can be screened by this method.

In the present invention, there is no particular limitation with respect to a method for screening a substance having the capability to regulate cytokine activity, in which a transformant of the present invention is used. For example, various substances can be added to a culture of cells transformed with the SIIS-1 gene, and changes, such as cell death, can be assessed to thereby screen a substance having the capability to regulate cytokine activity. By way of illustration, a clone of wild-type SIIS-1 (SH+) is cultured in the presence of LIF, and each of the sample substances is individually added to the cell culture. When cell death is observed, and when the features of apoptosis, such as chromatin condensation, are detected by a microscopic observation of stained cells, it can be concluded that the substance added to the cell culture has the ability to inhibit the activity of SIIS-1. In addition, a substance which delays or inhibits cell death of M1 cells or M1-Neo cells cultured in the presence of LIF can be considered to be a substance having the SIIS-1-like activity or SIIS-1 activity promoting activity and, therefore, such cultured cells can be also used for screening a novel pharmaceutical. Further, the cells transformed with the SIIS-1 gene can be cultured in the presence of various substances, and then, a substance having the capability to regulate cytokine activity can be assessed by using an anti-gp130 antibody or an anti-STAT3 antibody in combination with western blotting. By way of illustration, the cultured cells of SIIS-1 clone are stimulated with cytokines, such as IL-6, and the stimulated cells are cultured in the presence of a sample substance. Next, a cell lysate of the cultured cells is prepared, and immunoprecipitates with anti-gp130 antibody and with anti-STAT3 antibody are individually obtained. Subsequently, a western blotting of the thus obtained immunoprecipitates is performed with an anti-phosphotyrosine monoclonal antibody. The promotion of tyrosine phosphorylation of gp130 and STAT3 can be interpreted as an inhibition of SIIS-1 and, therefore, this method can be used for screening a substance having the SIIS-1 inhibitory activity.

BEST MODE FOR CARRYING OUT THE INVENTION

Hereinbelow, the present invention will be described in more detail with reference to the following Reference Example and Examples, but they should not be construed as limiting the scope of the present invention.

Reference Example 1

Cell Culture

In the Examples, cells were cultured by the following methods or substantially in accordance with the following methods.

Myeloid leukemia M1 cells were cultured in Eagle's minimal essential medium supplemented with double the normal concentrations of amino acids and vitamins, and 10% (vol/vol) fetal calf serum (FCS).

IL-6-dependent myeloma MH60 cells were maintained in RPMI 1640 medium supplemented with IL-6 (5 ng/ml) and 10% FCS.

IL-2/IL-4-dependent CT4S cells were cultured in RPMI 1640 medium supplemented with IL-4 (10 U/ml) and 10% FCS.

IL-3-dependent myeloid NFS60 cells were maintained in RPMI 1640 medium supplemented with 10% FCS and 10% conditioned medium from the culture of WEHI-3B cell line (murine myelomonocyte) as a source of IL-3.

Cells of M1 cell lines which constitutively express a dominant-negative form of STAT3 (M1-Y705F) {see Proc. Natl. Acad. Sci. USA 93, 3963–3966 (1996)} were cultured in substantially the same manner as used for culturing the parental M1 cells, except that the culture medium contained 250 µg/ml Geneticin (manufactured and sold by GIBCO BRL, USA).

Example 1

Preparation of SIIS-1, the Novel Protein of the Present Invention (1) Preparation of a Monoclonal Antibody Against the SH2 Domain of a STAT:

A monoclonal antibody against the amino acid sequence GTFLLRFS (Gly-Thr-Phe-Leu-Leu-Arg-Phe-Ser in 3-letter abbreviation) which is found in the SH2 domain and is highly conserved in proteins of the STAT family was produced as follows. The synthetic oligopeptide TKPPGTFLL-RFSESSKEG (SEQ ID NO: 6) (Thr-Lys-Pro-Pro-Gly-Thr-Phe-Leu-Leu-Arg-Phe-Ser-Glu-Ser-Ser-Lys-Glu-Gly in 3-letter abbreviation), corresponding to the 600th to 617th amino acids in the SH2 domain of STAT3, was coupled to keyhole limpet hemocyanin, and BALB/c mice were immunized therewith. Spleen cells from each of the immunized BALB/c mice were fused with mouse myeloma cells P3-X63-Ag8-653 to thereby establish a hybridoma clone FL-238, which produces a monoclonal antibody against the synthetic oligopeptide GTFLLRFS in which the N-terminus thereof is protected by Fmoc. The monoclonal antibody produced in the hybridoma clone was purified by protein A affinity chromatography from the ascitic fluid of BALB/c mice.

(2) Isolation of SIIS-1 cDNA:

Using the monoclonal antibody against the GTFLLRFS motif which was prepared in step (1) above, cDNAs comprising SH2 domains of STATs were isolated from a murine thymus cDNA library (Lambda ZAP; manufactured and sold by Stratagene Cloning Systems, USA) by means of PicoBlue Immunoscreening Kit (manufactured and sold by Stratagene Cloning Systems, USA). Particularly, 3 million plaques constituting the murine thymus cDNA library were screened in accordance with the instructions of the screening kit, and approximately 20 unknown genes (excluding the known genes, such as a gene encoding STAT3) were isolated.

The whole nucleotide sequences of 5 genes out of 20 isolated genes were determined. It was found that two genes contain an SH2 domain. One gene encodes a protein known as CIS (cytokine inducible SH2-containing protein), and the other gene encodes a novel protein having an amino acid sequence consisting of 212 amino acids, which contains an SH2 domain at the C-terminal region and a domain consisting of 8 contiguous serine residues at the N-terminal region. This novel protein was named "SIIS-1" (abbreviation for "STAT-induced inhibitor of STAT function-1").

(3) Construction of SIIS-1 Expression Vectors:

SIIS-1 cDNA isolated in step (2) above was digested with restriction enzymes XbaI and PvuII, and the end of the obtained restriction fragment (XbaI-PvuII) was converted into a blunt end. Then, the resultant blunt-ended fragment was inserted into the blunt-ended XbaI site of the mammalian expression vector pEF-BOS. Hereinafter, the constructed SIIS-1 expression vector is simply referred to as "pEF-BOS/SIIS-1 (SH+)".

For the construction of a mutant SIIS-1 which is an SH2 domain-deficient SIIS-1, a BssHII-digested fragment of 360 bp was removed from pEF-BOS/SIIS-1 (SH+). The thus obtained SIIS-1 expression vector (that is, a mutant SIIS-1 vector) which is deficient in the SH2 domain and is truncated at the C-terminus is hereinafter simply referred to as "pEF-BOS/SIIS-1 (SH−)".

Each of the expression vectors pEF-BOS/SIIS-1 (SH+) and pEF-BOS/SIIS-1 (SH−) prepared above was individually mixed with expression vector pSV2 Neo (encoding a neomycin-resistance gene) at a ratio of 20:1. Subsequently, each of the resultant vector mixtures was separately transfected into M1 cells by electroporation. Using neomycin resistance as an index, the transfectants (i.e., clones) were selected in the growth medium containing Geneticin (manufactured and sold by GIBCO BRL, USA) at 750 µg/ml.

Example 2

SIIS-1 Expression in Various Murine Tissues

A radiolabeled full-length cDNA of SIIS-1 as a probe was hybridized to mouse NTN blot membrane (manufactured and sold by CLONTECH, USA). As a control, a commercially available β-actin probe was used instead of the SIIS-1 probe. The results are shown in FIG. 3, wherein H indicates heart, B indicates brain, S indicates spleen, Lu indicates lung, L indicates liver, Sm indicates skeletal muscle, K indicates kidney and Te indicates testis.

The results show that SIIS-1 mRNA was ubiquitously expressed, and the expression was strong in lung, spleen and testis, and weak in all other tissues.

Example 3

Analysis of the Possible Induction of SIIS-1 in Factor-dependent Cell Lines

In the following analysis, cells were stimulated with the following cytokines: MH60 cells and M1 cells were stimulated with IL-6 (50 ng/ml) plus sIL-6R (5 ng/ml); IL-4-dependent CT4S cells were stimulated with IL-4 (10 U/ml) plus IL-2 (10 ng/ml); and G-CSF-dependent NFS60 cells were stimulated with G-CSF (20 ng/ml) plus IL-3 (5 ng/ml).

With respect to all of the cell lines excluding M1 cells, the cells were factor-depleted for 4 hours in RPM1 1640 medium containing 1% BSA, and subsequently, the cells were stimulated with the above-mentioned cytokines by culturing in a cytokine-containing medium for various periods of time (min.) shown in FIG. 4. With respect to M1 cells, the cells were cultured in the same manner as described in Reference Example 1, and subsequently, the cells were stimulated with the above-mentioned cytokines by culturing the cells in a cytokine-containing medium for various periods of time (min.) shown in FIG. 4.

Cytoplasmic RNA was extracted from each of the cytokine-stimulated cells using Iso-Gen (manufactured and sold by Nippon Gene Co. Ltd., Japan). The extracted total RNA (5 µg/ml) was electrophoresed on agarose gel, and then, the RNA was transferred to a nylon membrane (Hybond N+; manufactured and sold by Amersham International, England). The resultant membrane was hybridized separately with radiolabeled probes, namely, the SIIS-1 probe, and the commercially available β-actin probe and c-myc probe. The results are shown in FIG. 4.

Figure 4:
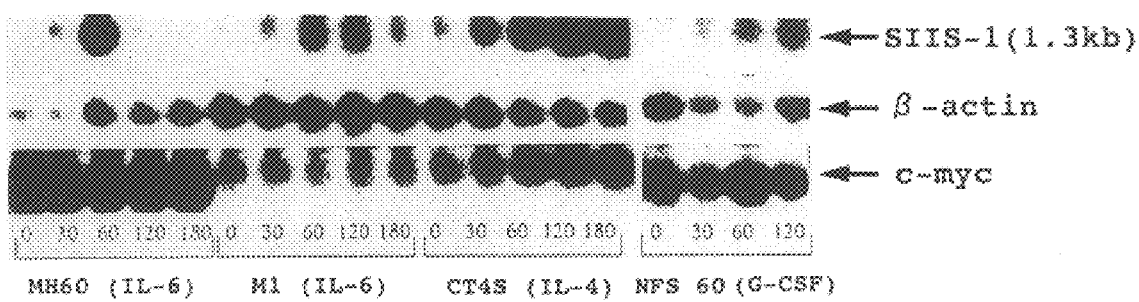
FIG. 4 shows the induction of SIIS-1 mRNA in factor-dependent cells.

As shown in FIG. 4, MH60 cells and M1 cells both expressed SIIS-1 mRNA, with the expression peaking 60 to 120 minutes after the treatment with IL-6 plus sIL-6R. CT4S cells and NSF60 cells expressed SIIS-1 mRNA in response to IL-4 and G-CSF, respectively. These results show that SIIS-1 is induced not only by IL-6 and G-CSF, both of which activate STAT3, but also by IL-4, a cytokine which activates STAT6.

Example 4

Analysis of SIIS-1 Induction in M1 Cells Transfected with Wild-type STAT3 Gene or Y705F Gene M1 cells transfected with wild-type STAT3 gene (hereinafter, frequently referred to as "M1-STAT3"), and M1 cells transfected with a dominant-negative form of STAT3 gene (hereinafter, frequently referred to as "M1-Y705F") were used in the following analysis. The dominant-negative form of STAT3 is a mutant STAT3 in which a tyrosine (Y) at residue 705 (which is phosphorylated by a JAK kinase) is substituted with phenylalanine (F) by point mutation. As a control, transfectants containing only the neomycin-resistance gene (hereinafter, frequently referred to as "M1-Neo") were used.

Figure 5:
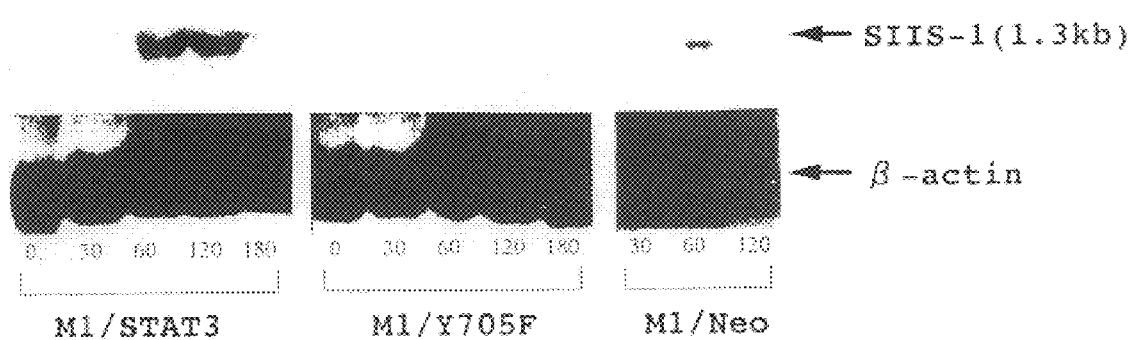
FIG. 5 shows the induction of SIIS-1 mRNA in M1 cells transfected with wild-type STAT3 gene and M1 cells transfected with a dominant-negative form of STAT3 gene.

Each of the above-mentioned cells was individually stimulated with 1,000 U/ml of LIF in substantially the same manner as mentioned in Example 3 for various periods of time (min) shown in FIG. 5. Subsequently, the extraction of cytoplasmic RNA and northern blotting were performed in substantially the same manner as mentioned in Example 3, except that the SIIS-1 probe and the β-actin probe were used as the hybridization probes. The results are shown in FIG. 5.

SIIS-1 mRNA was more strongly induced by LIF in M1-STAT3 cells than in control M1-Neo cells, but was not induced in M1-Y705F cells. These results indicate that the SIIS-1 gene is one of the target genes for STAT3 and the expression thereof is induced by the JAK/STAT signalling pathway.

Example 5

Analyses of the Effect of SIIS-1 on the gp130 -transduced Signalling Pathway

The M1 transfectant expressing the wild-type SIIS-1 (SH+), the M1 transfectant expressing the mutant SIIS-1 (SH−) (both M1 transfectants were obtained in the same manner as mentioned in Example 1), the parental M1 cells and the M1-Neo cells were individually used in the following analyses.

Figure 6:
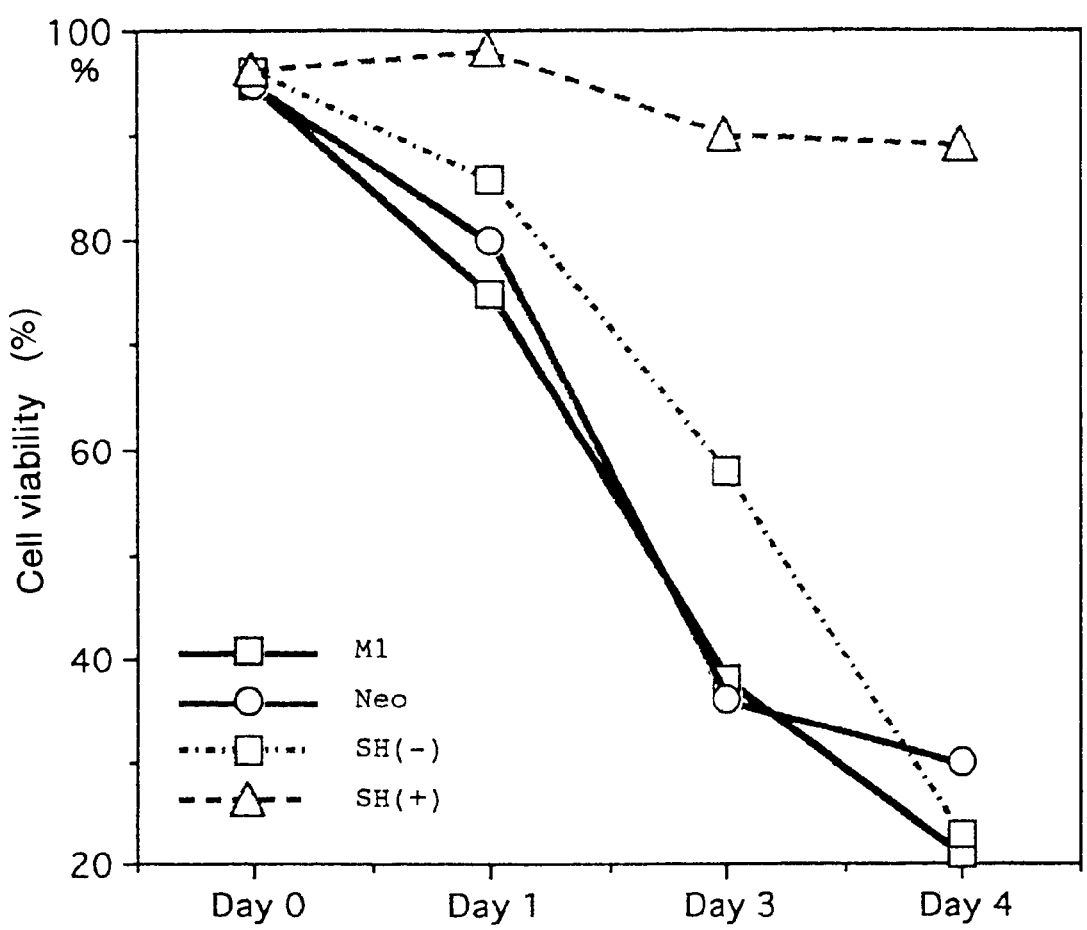
FIG. 6 shows the viability of M1 cells transfected with wild-type SIIS-1 gene and M1 cells transfected with a mutant SIIS-1 gene, both after stimulation with LIF.

Each of the above-mentioned four types of cell lines were individually used. A medium containing LIF (1,000 U/ml) was seeded with the cell line (on day 0) and the cells were cultured for 1 to 4 days. The viability of the cells in each culture was assessed on days 0, 1, 3 and 4 in accordance with the method described in Saibo Meneki Jikken Sousahou (Experimental Methods for Cell Immunology) (Barbara B. Mishell et al. ed., Rikogakusha, pp. 15–16, 1982). The results are shown in FIG. 6.

Figure 7:
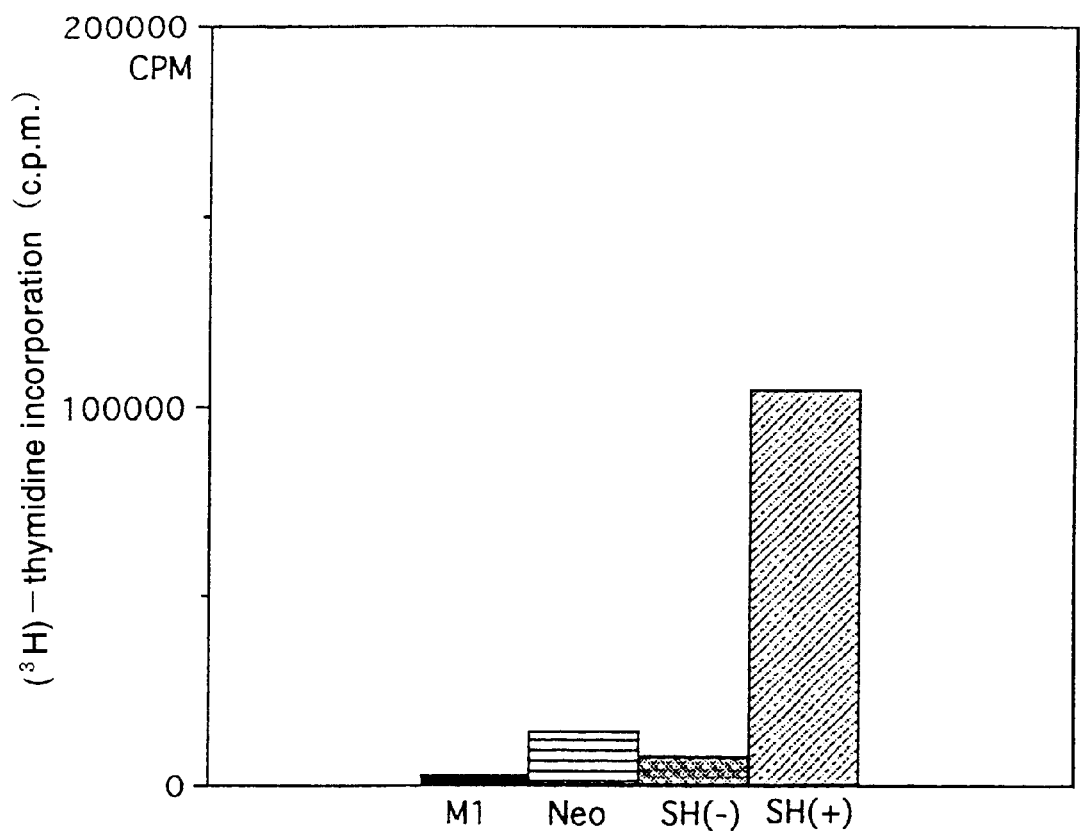
FIG. 7 shows [$^3$H]-thymidine incorporation by M1 cells transfected with wild-type SIIS-1 gene and M1 cells transfected with a mutant SIIS-1 gene, both measured on day 1 after stimulation with LIF.

Further, on day 1 after the stimulation with LIF, the amount of [$^3$H]-thymidine incorporation by the cells was measured in accordance with the method described in Zoku- Seikagaku Jikken Kouza 5 Menekiseikagakuhou (Experiments in Biochemistry, second series, vol. 5, Immunobiochemical Methods) (p. 198, Nippon Seikagakukai ed., Tokyo Kagaku Dojinsha, 1986). The results are shown in FIG. 7.

Figure 8:
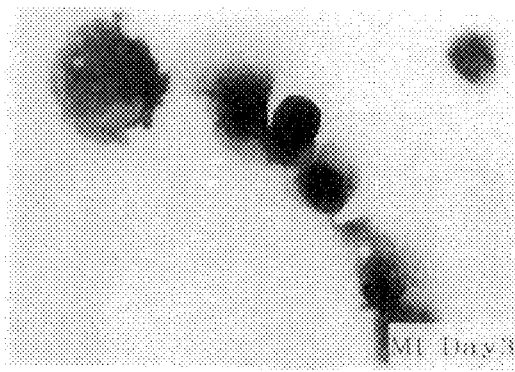
FIG. 8(a) shows the May-Grunwald-Giemsa staining of parental M1 cells on day 3 after stimulation with LIF.
FIG. 8(b) shows the May-Grunwald-Giemsa staining of M1-Neo cells on day 3 after stimulation with LIF.
FIG. 8(c) shows the May-Grunwald-Giemsa staining of M1 cells transfected with a mutant SIIS-1 (SH−) gene on day 3 after stimulation with LIF.
FIG. 8(d) shows the May-Grunwald-Giemsa staining of M1 cells transfected with wild-type SIIS-1 (SH+) gene on day 3 after stimulation with LIF.
Figure 8:
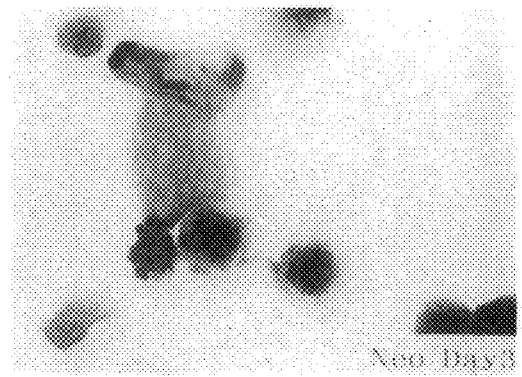
Figure 8:
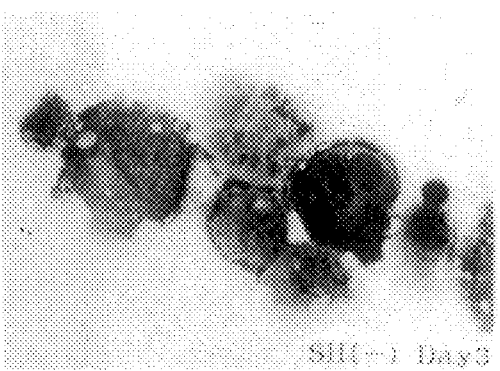
Figure 8:

In addition, the cells cultured for 3 days in the above-mentioned manner were stained by May-Grunwald-Giemsa staining, and the stained cells were observed under an optical microscope. The results are shown in FIG. 8.

In FIGS. 6, 7 and 8(a) to (d), "M1" represents parental M1 cells, "Neo" represents M1-Neo cells, "SH(−)" represents M1 cells expressing an SH2-domain-deficient mutant SIIS-1, and "SH(+)" represents M1 cells expressing wild-type SIIS-1.

As shown in FIG. 6, M1-Neo cells and SH(−) cells suffered growth arrest and cell death after the stimulation with LIF, as did the parental M1 cells. The dead cells showed the features of apoptosis, such as chromatin condensation and apoptotic bodies {see FIGS. 8(a), (b) and (c)}. In contrast, the growth arrest of SH(+) cells did not occur following the stimulation with LIF {see FIGS. 6, 7 and 8(d)}. These results suggest that SIIS-1 blocks the gp130-transduced signalling pathway, and the SH2 domain of SIIS-1 is required for this blocking of the signals.

Example 6

Analysis of the Inhibitory Mechanism of SIIS-1 in the gp130-transduced Signalling Pathway The M1 transfectants expressing the wild-type SIIS-1 (SH+), the M1 transfectants expressing the mutant SIIS-1 (SH−) (both M1 transfectants were obtained in the same manner as mentioned in Example 1), the parental M1 cells and the M1-Neo cells were individually used in the following analysis.

Cells ($5 \times 10^7$ cells) were stimulated with IL-6 (1 μg/ml) plus sIL-6R (1 μg/ml) for 5 minutes. As a control, untreated cells (stimulation: 0 min.) were used. Subsequently, the cells were solubilized with lysis buffer (0.5% Nonidet P-40, 10 mM Tris.Cl, pH 7.4, 150 mM NaCl, 1 mM EDTA, 1 mM $Na_3VO_4$) containing protease inhibitors, thereby obtaining a cell lysate. The obtained cell lysate was reacted with anti-gp130 antibody (manufactured and sold by Upstate Biotechnology, USA) to obtain an immunoprecipitate containing gp130. The above operations were also conducted using anti-STAT3 antibody instead of the anti-gp130 antibody, to thereby obtain an immunoprecipitate containing STAT3. The thus obtained immunoprecipitates were resolved by SDS-PAGE. Immunoblotting of the resolved immunoprecipitates was performed using anti-phosphotyrosine monoclonal antibody (4G10; manufactured and sold by Upstate Biotechnology, USA) as a probe. The anti-phosphotyrosine antibody which associated with the immunoprecipitates was visualized with chemiluminescence system (manufactured and sold by Amersham International, England). The results are shown in FIG. 9.

Figure 9:
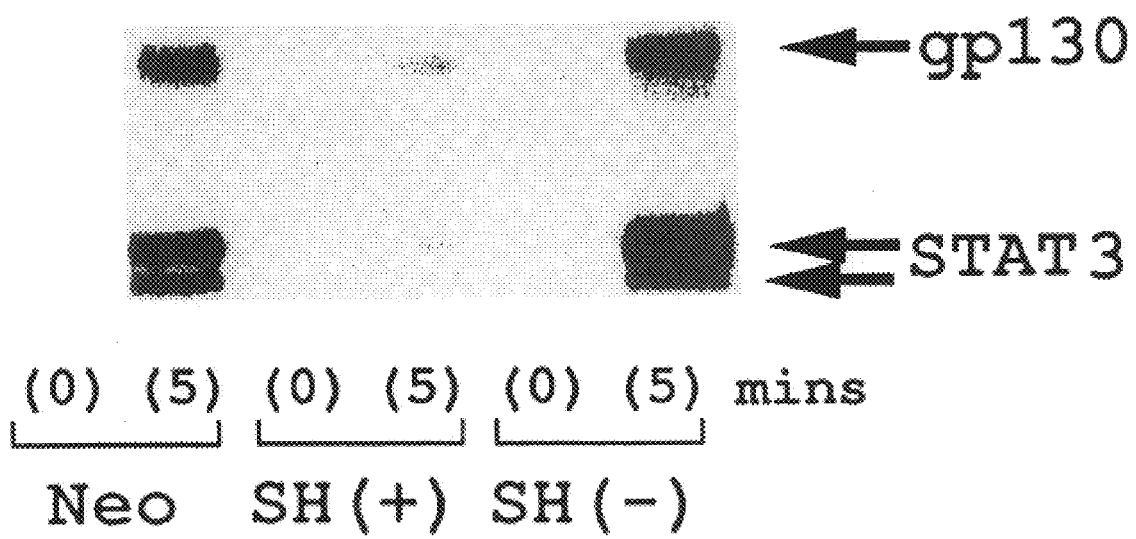
FIG. 9 shows the IL-6-induced tyrosine phosphorylation of gp130 and STAT3 in M1 cells transfected with wild-type SIIS-1 gene and M1 cells transfected with a mutant SIIS-1 gene.

FIG. 9 shows the immunoblots of the immunoprecipitate obtained with anti-gp130 antibody and the immunoprecipitate obtained with anti-STAT3 antibody, both probed with the anti-phosphotyrosine antibody. As apparent from FIG. 9, tyrosine phosphorylation of gp130 and STAT3 was much reduced in the SH(+) cells, as compared to those in the control M1-Neo cells and the SH(−) cells.

In Table 1 below, the characteristics of SIIS-1 of the present invention which have become apparent from Examples 1 to 6 above are shown, in comparison with those of CIS which is a protein known to participate in an intracellular signalling pathway.

TABLE 1

Comparisons between SIIS-1 and CIS

|  | SIIS-1 | CIS |
|---|---|---|
| Length of whole protein (no. of a.a.) | 212 a.a. | 257 a.a. |
| Cytokines which induce expression | IL-6, LIF, G-CSF, IL-4 | IL-2, IL-3, GM-CSF, EPO |
| STATs which induce expression | STAT3, STAT6 | STAT5 |
| STATs which are inhibited | STAT3 | STAT5 |
| Presence or absence of an SH2 domain | present (79th a.a. to 167th a.a.; Homology to the SH2 domain of CIS: 36%) | present |
| Presence or absence of an SH3 domain | absent | absent |
| Activity mechanism | Inhibit tyrosine phosphorylation of STAT and receptors → Suppress STAT function | Bind to STAT5-binding region of tyrosine phosphorylated receptor via SH2 domain → Inhibit STAT5 binding → Suppress STAT5 function |
| Activity | Inhibit LIF-mediated apoptosis Inhibit LIF-mediated growth arrest Suppress macrophage differentiation of M1 cells | Inhibit IL-3, EPO-dependent cell proliferation |
| Expression sites | Strong: lung, spleen, testis Weak: other tissues | Strong: kidney, lung, liver Weak: stomach, heart None: brain, spleen |

INDUSTRIAL APPLICABILITY

By the use of the SIIS-1 protein and the transformant of the present invention, it has become possible to screen a novel substance having the capability to regulate cytokine activity. Further, by the use of the genetic information of SIIS-1 disclosed in the present invention, it has become possible to design SIIS-1-specific antisense DNA and RNA. The substance having the capability to regulate cytokine activity and the antisense DNA and RNA can be used as a potentiator for endogenous or administered cytokines having pharmacological effects.

By the use of the SIIS-1-specific monoclonal antibody, it has become possible to construct a system for performing ELISA or RIA, or western blotting to detect the SIIS-1 protein in a cell or a tissue. Further, by the use of the DNA or RNA probe specific for the SIIS-1 mRNA, it has become possible to detect the expression of the SIIS-1 gene in a cell or a tissue. These systems can be used for diagnoses.

What is claimed is:

1. A substantially pure protein having the following characteristics:
  (1) said protein is induced by STAT3 or STAT6;
  (2) said protein inhibits tyrosine phosphorylation of gp130 and STAT3;
  (3) said protein comprises an SH2 domain; and
  (4) said protein comprises the amino acid sequence of SEQ ID NO: 2.

2. An isolated DNA coding for a protein having the following characteristics:
  (1) said protein is induced by STAT3 or STAT6;
  (2) said protein inhibits tyrosine phosphorylation of gp130 and STAT3;
  (3) said protein comprises an SH2 domain; and
  (4) said protein comprises the amino acid sequence of SEQ ID NO: 2.

3. The DNA according to claim 4, wherein said nucleotide sequence has the nucleotide sequence of SEQ ID NO: 1.

4. A method for screening a substance for activity of regulating a cytokine activity, comprising:
  contacting a sample comprising said substance with the protein of claim 1; and
  assessing the activation or inhibition of said protein by said sample;

wherein activity of said substance of regulating a cytokine activity is indicated by activation or inhibition of said protein.

5. A replicable recombinant DNA molecule, comprising a replicable expression vector and, operably inserted therein, the DNA of claim 2.

6. A cell of a microorganism or cell culture, transformed with the replicable recombinant DNA of claim 5.

7. A method for screening a substance for activity of regulating a cytokine activity, comprising:

contacting a sample comprising said substance with the transformed cell of a microorganism or cell culture of claim 6; and assessing the activation or inhibition of a protein by said sample, wherein the protein is encoded by the replicable recombinant DNA molecule in said transformed cell;

wherein activity of said substance of regulating a cytokine is indicated by activation or inhibition of said protein.

8. The method of claim 4, wherein activity of said substance of regulating the activity of the protein comprising the amino acid sequence of SEQ. ID. NO. 2 is indicated by activation or inhibition of said protein.

9. The method of claim 7, wherein activity of said substance of regulating the activity of the protein comprising the amino acid sequence of SEQ. ID. NO. 2 is indicated by activation or inhibition of said protein.

10. An isolated protein having the amino acid sequence of SEQ ID NO:2.

11. An isolated DNA having the nucleotide sequence of SEQ ID NO:1.

* * * * *

SEQUENCE LISTING

<160> NUMBER OF SEQ ID NOS: 6

<210> SEQ ID NO 1
<211> LENGTH: 1087
<212> TYPE: DNA
<213> ORGANISM: Mus sp.
<220> FEATURE:
<221> NAME/KEY: CDS
<222> LOCATION: (16)..(651)

<400> SEQUENCE: 1

```
ggcccctcga gtagg atg gta gca cgc aac cag gtg gca gcc gac aat gcg        51
            Met Val Ala Arg Asn Gln Val Ala Ala Asp Asn Ala
              1               5                  10 atc tcc ccg gca gca gag ccc cga cgg cgg tca gag ccc tcc tcg tcc         99
Ile Ser Pro Ala Ala Glu Pro Arg Arg Arg Ser Glu Pro Ser Ser Ser
         15                  20                  25 tcg tct tcg tcc tcg cca gcg gcc ccc gtg cgt ccc cgg ccc tgc ccg        147
Ser Ser Ser Ser Ser Pro Ala Ala Pro Val Arg Pro Arg Pro Cys Pro
     30                  35                  40 ggg gtc cca gcc cca gcc cct ggc gac act cac ttc cgc acc ttc cgc        195
Gly Val Pro Ala Pro Ala Pro Gly Asp Thr His Phe Arg Thr Phe Arg
 45                  50                  55                  60 tcc cac tcc gat tac cgg cgc atc acg cgg acc agc gcg ctc ctg gac        243
Ser His Ser Asp Tyr Arg Arg Ile Thr Arg Thr Ser Ala Leu Leu Asp
                 65                  70                  75 gcc tgc ggc ttc tat tgg gga ccc ctg agc gtg cac ggg gcg cac gag        291
Ala Cys Gly Phe Tyr Trp Gly Pro Leu Ser Val His Gly Ala His Glu
             80                  85                  90 cgg ctg cgt gcc gag ccc gtg ggc acc ttc ttg gtg cgc gac agt cgc        339
Arg Leu Arg Ala Glu Pro Val Gly Thr Phe Leu Val Arg Asp Ser Arg
         95                 100                 105 caa cgg aac tgc ttc ttc gcg ctc agc gtg aag atg gct tcg ggc ccc        387
Gln Arg Asn Cys Phe Phe Ala Leu Ser Val Lys Met Ala Ser Gly Pro
     110                 115                 120 acg agc atc cgc gtg cac ttc cag gcc ggc cgc ttc cac ttg gac ggc        435
Thr Ser Ile Arg Val His Phe Gln Ala Gly Arg Phe His Leu Asp Gly
125                 130                 135                 140 aac cgc gag acc ttc gac tgc ctt ttc gag ctg ctg gag cac tac gtg        483
Asn Arg Glu Thr Phe Asp Cys Leu Phe Glu Leu Leu Glu His Tyr Val
                145                 150                 155 gcg gcg ccg cgc cgc atg ttg ggg gcc ccg ctg cgc cag cgc cgc gtg        531
Ala Ala Pro Arg Arg Met Leu Gly Ala Pro Leu Arg Gln Arg Arg Val
            160                 165                 170 cgg ccg ctg cag gag ctg tgt cgc cag cgc atc gtg gcc gcc gtg ggt        579
Arg Pro Leu Gln Glu Leu Cys Arg Gln Arg Ile Val Ala Ala Val Gly
        175                 180                 185 cgc gag aac ctg gcg cgc atc cct ctt aac ccg gta ctc cgt gac tac        627
Arg Glu Asn Leu Ala Arg Ile Pro Leu Asn Pro Val Leu Arg Asp Tyr
    190                 195                 200 ctg agt tcc ttc ccc ttc cag atc tgaccggctg ccgctgtgcc gcagcattaa       681
Leu Ser Ser Phe Pro Phe Gln Ile
205                 210 gtgggggcgc cttattattt cttattatta attattatta tttttctgga accacgtggg      741
agccctcccc gcctgggtcg gagggagtgg ttgtggaggg tgagatgcct cccacttctg      801
gctggagacc tcatcccacc tctcaggggt gggggtgctc ccctcctggt gctccctccg      861 ggtccccccct ggttgtagca gcttgtgtct ggggccagga cctgaattcc actcctacct    921
```

```
ctccatgttt acatattccc agtatctttg cacaaaccag gggtcgggga gggtctctgg      981 cttcatttt  ctgctgtgca gaatatccta ttttatattt ttacagccag tttaggtaat     1041
aaactttatt atgaaagttt ttttttaaaa gaaacaaaca aagatt                    1087
```

<210> SEQ ID NO 2
<211> LENGTH: 212
<212> TYPE: PRT
<213> ORGANISM: Mus sp.

<400> SEQUENCE: 2

```
Met Val Arg Asn Gln Val Ala Ala Asp Asn Ala Ile Ser Pro Ala
 1               5                  10                  15

Ala Glu Pro Arg Arg Ser Glu Pro Ser Ser Ser Ser Ser Ser
                20                  25                  30

Ser Pro Ala Ala Pro Val Arg Pro Arg Pro Cys Pro Gly Val Pro Ala
                35                  40                  45

Pro Ala Pro Gly Asp Thr His Phe Arg Thr Phe Arg Ser His Ser Asp
    50                  55                  60

Tyr Arg Arg Ile Thr Arg Thr Ser Ala Leu Leu Asp Ala Cys Gly Phe
65                  70                  75                  80

Tyr Trp Gly Pro Leu Ser Val His Gly Ala His Glu Arg Leu Arg Ala
                85                  90                  95

Glu Pro Val Gly Thr Phe Leu Val Arg Asp Ser Arg Gln Arg Asn Cys
                100                 105                 110

Phe Phe Ala Leu Ser Val Lys Met Ala Ser Gly Pro Thr Ser Ile Arg
            115                 120                 125

Val His Phe Gln Ala Gly Arg Phe His Leu Asp Gly Asn Arg Glu Thr
    130                 135                 140

Phe Asp Cys Leu Phe Glu Leu Leu Glu His Tyr Val Ala Ala Pro Arg
145                 150                 155                 160

Arg Met Leu Gly Ala Pro Leu Arg Gln Arg Arg Val Arg Pro Leu Gln
                165                 170                 175

Glu Leu Cys Arg Gln Arg Ile Val Ala Ala Val Gly Arg Glu Asn Leu
            180                 185                 190

Ala Arg Ile Pro Leu Asn Pro Val Leu Arg Asp Tyr Leu Ser Ser Phe
        195                 200                 205

Pro Phe Gln Ile
    210
```

<210> SEQ ID NO 3
<211> LENGTH: 96
<212> TYPE: PRT
<213> ORGANISM: cytokine inducible SH2-containing protein

<400> SEQUENCE: 3

```
Trp Tyr Trp Gly Ser Ile Thr Ala Ser Glu Ala Arg Gln His Leu Gln
 1               5                  10                  15

Lys Met Pro Glu Gly Thr Phe Leu Val Arg Asp Ser Thr His Pro Ser
                20                  25                  30

Tyr Leu Phe Thr Leu Ser Val Lys Thr Thr Arg Gly Pro Thr Asn Val
            35                  40                  45

Arg Ile Glu Tyr Ala Asp Ser Ser Phe Arg Leu Asp Ser Asn Cys Leu
    50                  55                  60

Ser Arg Pro Arg Ile Leu Ala Phe Pro Asp Val Val Ser Leu Val Gln
65                  70                  75                  80
```

```
His Tyr Val Ala Ser Cys Ala Ala Asp Thr Arg Ser Asp Ser Pro Asp
                85                  90                  95

<210> SEQ ID NO 4
<211> LENGTH: 95
<212> TYPE: PRT
<213> ORGANISM: Mus sp.
<220> FEATURE:
<221> NAME/KEY: UNSURE
<222> LOCATION: (1)..(95)
<223> OTHER INFORMATION: Xaa = any amino acid, unknown or other

<400> SEQUENCE: 4

Gly Phe Tyr Trp Gly Pro Leu Ser Val His Gly Ala His Glu Arg Leu
  1               5                  10                  15

Arg Ala Glu Pro Val Gly Thr Phe Leu Val Arg Asp Ser Arg Gln Arg
                20                  25                  30

Asn Cys Phe Phe Ala Leu Ser Val Lys Met Ala Ser Gly Pro Thr Ser
                35                  40                  45

Ile Arg Val His Phe Gln Ala Gly Arg Phe His Leu Asp Gly Asn Xaa
        50                  55                  60

Xaa Xaa Xaa Xaa Arg Glu Xaa Thr Phe Asp Cys Leu Phe Glu Leu Leu
 65                  70                  75                  80

Glu His Tyr Val Ala Ala Pro Arg Arg Met Leu Gly Ala Pro Leu
                85                  90                  95

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: synthetic
      oligopeptide

<400> SEQUENCE: 5

Gly Thr Phe Leu Leu Arg Phe Ser
  1               5

<210> SEQ ID NO 6
<211> LENGTH: 18
<212> TYPE: PRT
<213> ORGANISM: Artificial Sequence
<220> FEATURE:
<223> OTHER INFORMATION: Description of Artificial Sequence: synthetic
      oligopeptide

<400> SEQUENCE: 6

Thr Lys Pro Pro Gly Thr Phe Leu Leu Arg Phe Ser Glu Ser Ser Lys
  1               5                  10                  15

Glu Gly
```